Figure 1:
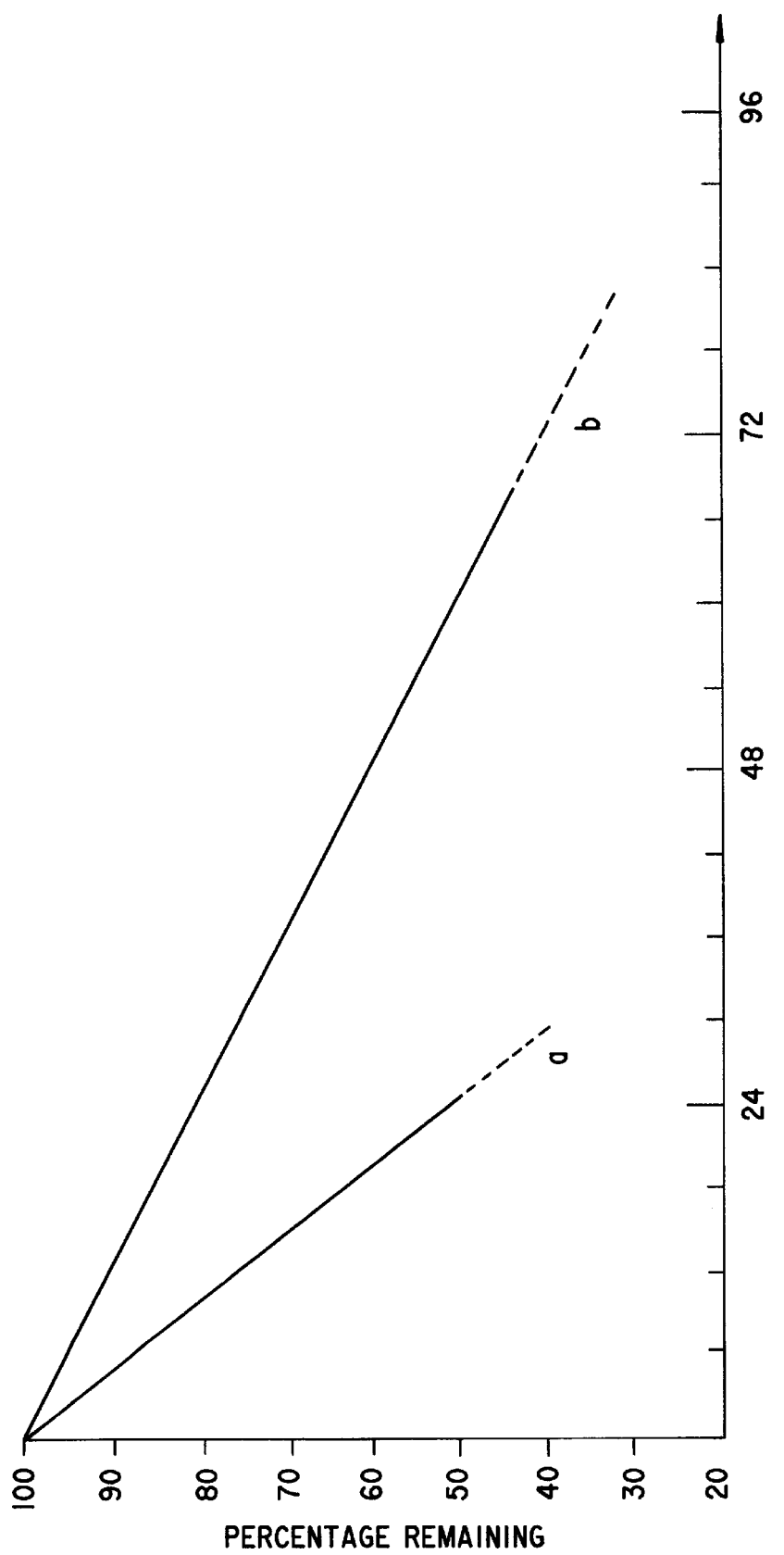

United States Patent [19]
Nofre et al.

[11] Patent Number: 5,773,640
[45] Date of Patent: Jun. 30, 1998

[54] N-[N-(3,3-DIMETHYLBUTYL)-L-A-ASPARTYL]-L-HEXAHYDROPHENYLALANINE 1-METHYL ESTER USEFUL AS A SWEETENING AGENT, ITS METHOD OF PREPARATION

[76] Inventors: Claude Nofre, 119 Cours Albert Thomas, 69003 Lyons; Jean-Marie Tinti, 5 Impasse de la Drelatière, 69680 Chassieu, both of France

[21] Appl. No.: 737,138
[22] PCT Filed: May 5, 1995
[86] PCT No.: PCT/FR95/00588
  § 371 Date: Nov. 7, 1996
  § 102(e) Date: Nov. 7, 1996
[87] PCT Pub. No.: WO95/30688
  PCT Pub. Date: Nov. 16, 1995

[30] Foreign Application Priority Data

May 9, 1994 [FR] France .................................. 94 05675

[51] Int. Cl.$^6$ .................................................. C07C 229/00
[52] U.S. Cl. ............................................................. 560/125
[58] Field of Search ............................................. 560/125

[56] References Cited

U.S. PATENT DOCUMENTS 5,510,508  4/1996  Claude et al. ........................... 560/125

*Primary Examiner*—Joseph Conrad
*Attorney, Agent, or Firm*—Armstrong, Westerman, Hattori, McLeland & Naughton

[57] ABSTRACT

Novel sweetening compound characterized in that it is N-[N-(3,3-dimethylbutyl)-L-$\alpha$-aspartyl]-L-hexahydrophenylalanine 1-methyl ester of formula:

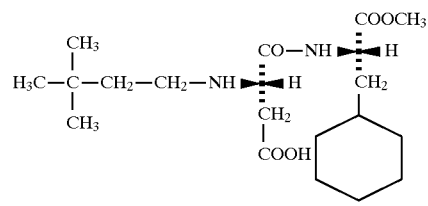

and its method of preparation characterized in that an aqueous/alcohol solution of pH 4.5–5 of aspartame and 3,3-dimethylbutyraldehyde at room temperature is treated with hydrogen at a pressure of 3 bars in the presence of a catalyst based on platinum such as platinum black and platinum oxide and in that the product formed is purified by precipitation and filtration after evaporation in vacuo of the alcohol part of the solvent.

17 Claims, 2 Drawing Sheets

N-[N-(3,3-DIMETHYLBUTYL)-L-A-ASPARTYL]-L-HEXAHYDROPHENYLALANINE 1-METHYL ESTER USEFUL AS A SWEETENING AGENT, ITS METHOD OF PREPARATION

The present invention relates to a novel compound useful as a sweetening agent, as well as its method of preparation.

This novel compound is particularly useful for sweetening a variety of products, especially drinks, foods, confectionery, pastries, chewing gums, hygiene products and toiletries, as well as cosmetic, pharmaceutical and veterinary products.

It is known that, in order to be usable on an industrial scale, a sweetening agent must possess firstly an intense sweetening potency, making it possible to limit the cost of use, and secondly a satisfactory stability, i.e. a stability compatible with the conditions of use.

Amongst the sweetening agents currently on the market, the dipeptide derivative N-L-α-aspartyl-L-phenylalanine 1-methyl ester, known by the name aspartame and having the following formula:

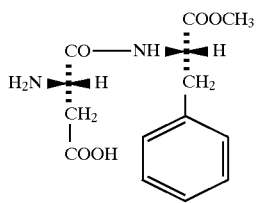

is the most widely used at the present time (U.S. Pat. No. 3,492,131). The sweetening potency of aspartame is relatively low, since it is less than 200 times that of sucrose on a weight basis. Despite its excellent organoleptic properties, the main disadvantages of this compound are that it is an expensive product on account of its relatively low sweetening intensity, and that it has a rather low stability under certain conditions of use of sweetening agents, especially in neutral media, limiting its areas of industrial application.

Consequently the food industry has an apparent need for a new sweetening agent which has a high sweetening activity, so as to reduce its cost price, and which is as least as stable as aspartame and even more stable than aspartame, especially in neutral media.

In a first aspect, the invention relates to a novel sweetening agent, N-[N(3,3-dimethylbutyl)-L-α-aspartyl]-L-hexahydrophenylalanine 1-methyl ester of the formula:

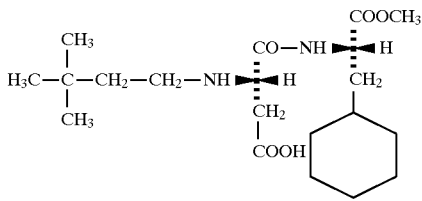

This novel sweetening compound is therefore an N-alkylated derivative of a hexahydrogenated compound of aspartame (hexahydroaspartame).

Hexahydroaspartame, of formula:

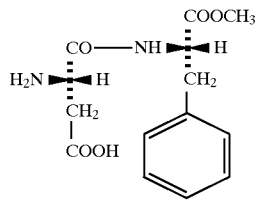

has already been described in the literature and especially in the French Pat. FR 2 013 158. Its sweetening potency, quite similar to that of aspartame, is about 225 times that of sucrose on a weight basis.

It has been discovered, quite unexpectedly, that the compound of the invention is, on a weight basis, around 50 (fifty) times sweeter than aspartame and 12,000 (twelve thousand) times sweeter than sucrose (table sugar).

Moreover, it has been observed that the stability of the compound of the invention is much higher than that of aspartame under the common conditions of use for the food preparations. This advantage is all the more important because one of the limits of the use of aspartame in certain food preparations originates from its very low stability in media near to neutrality, i. e. for values of pH of about 7, values of pH which are frequently encountered in products such as dairy products, pastries or other preparations needing a high cooking temperature, chewing gums and toothpastes.

Although obtained directly from aspartame, the compound of the invention possesses the advantage in that it does not contain L-phenylalanine, the phenyl group of this amino acid being reduced to a cyclohexyl group in the compound of the invention. Moreover, due to the very high sweetening potency of the compound of the invention, its use in the food products will take place with concentrations 60 times less than those of aspartame. Consequently, in the food products, the presence, often debated, of certain constituents of aspartame, namely the presence of methanol or L-phenylalanine, will respectively be very greatly reduced or supressed by the use of the compound of the present invention.

The aim of the present patent application is to cover the compound of the invention as a sweetening agent, and also to cover the sweetening compositions incorporating by way of sweetening compositions the compound of the invention as well as the use of this compound for sweetening the various products referred to in the introduction.

The sweetening agent of the present invention may be added to any edible product to which it is desired to give a sweet taste, provided that it is added in sufficient proportions to attain the level of sweetness desired. The optimal use concentration of the sweetening agent will depend upon a variety of factors such as, for example, the conditions of storage and use of the products, the particular constituents of the products and the level of sweetness desired. Any qualified person can easily determine the optimal proportion of sweetening agent which must be employed in order to obtain an edible product by carrying out routine sensory analyses. The sweetening agent of the present invention is, in general, added to the edible products in proportions ranging from 0.5 mg to 50 mg of sweetening agent per kilogramme or per litre of edible product. The concentrated products will obviously contain greater quantities of sweetening agent, and will then be diluted following the final intentions of use.

The sweetening agent of the present invention may be added in the pure form to products to be sweetened, but because of its high sweetening potency it is generally mixed with an appropriate carrier or bulking agent.

Advantageously, the appropriate carriers or bulking agents are selected from the group consisting of polydextrose, starch, maltodextrins, cellulose, methylcellulose, carboxymethylcellulose and other derivatives of cellulose, sodium alginate, pectins, gums, lactose, maltose, glucose, leucine, glycerol, mannitol, sorbitol, sodium bicarbonate, phosphoric, citric, tartaric, fumaric, benzoic, sorbic and propionic acids and their sodium, potassium and calcium salts, and equivalents thereof.

The sweetening agent of the invention may, in an edible product, be employed as the only sweetening agent, or in combination with other sweetening agents such as sucrose, corn syrup, fructose, sweet dipeptide analogues or derivatives (aspartame, alitame), neohesperidin dihydrochalcone, hydrogenated isomaltulose, stevioside, the L sugars, glycyrrhizin, xylitol, sorbitol, mannitol, acesulfame, saccharin and its sodium, potassium, ammonium and calcium salts, cyclamic acid and its sodium, potassium and calcium salts, sucralose, monellin, thaumatin and equivalents thereof.

In a second aspect, the invention concerns the method of preparation of the precited compound, method which is characterized in that a solution of aspartame and 3,3-dimethylbutyraldehyde at room temperature is treated with hydrogen at a relative pressure of 3 bars (0.3 MPa) in the presence of a catalyst based on platinum.

In one advantageous embodiment of this method, the precited catalyst is selected from the group comprising platinum black and platinum oxide.

The monitoring of the progress of the reaction by taking a sample and evaluating the formed product by high performance liquid chromatography (H.P.L.C.) permits the person of the art to easily determine the hydrogenation time appropriate to the conditions employed.

In one currently preferred method of the invention, the solution of aspartame and 3,3-dimethylbutyraldehyde is an aqueous/alcohol solution of pH 4.5–5 obtained by mixing a 0.1M acetic acid solution and methanol, the concentration of aspartame in the aqueous/alcohol solvent being between 50 and 60 g/l and the concentration of 3,3-dimethylbutyraldehyde between 20 and 30 g/l.

In an advantageous aspect of the invention, the formed product is purified by precipitation and filtration after evaporation in vacuo of the alcohol part of the solvent.

The compound of the invention can also be obtained from other methods. The N-L-α-aspartyl-L-hexahydrophenylalanine 1-methyl ester can in particular be submitted to a reductive N-alkylation with 3,3-dimethylbutyraldehyde under the action of sodium cyanoborohydride or hydrogen in the presence of catalysts (see for example Ohfune et al., Chem. Letters, 1984, pp. 441–444 and the review of P. N. Rylander, "Catalytic Hydrogenation in Organic Synthesis", Academic Press, San Diego, 1993, pp. 165–174).

The method of the invention is however much more advantageous in that it permits obtaining the novel sweetening compound directly, and in one sole step, from aspartame. This method in effect permits the simultaneous carrying out of the reductive N-alkylation by the 3,3-dimethylbutyraldehyde and the hydrogenation of the phenyl group of aspartame to give the cyclohexyl group.

However, the simultaneous carrying out of the reductive N-alkylation and the hydrogenation of the phenyl group has only proved to be possible for a limited number of catalysts and under very specific experimental conditions which alone permit obtaining the high analytic purity necessary, of the compound being the object of the invention, for use in foods.

It should be noted that the use of aspartame as starting material in the preparation of the compound of the invention has necessitated the resolving of certain difficulties connected to the properties of aspartame.

In effect, aspartame possesses a relatively low solubility in most organic solvents; its solubility is in general less than a few grammes per liter.

In other respects, if the solubility of aspartame is greater in aqueous media, its stability is however relatively low in these media.

Moreover, any attempt to raise the temperature with the aim of improving the solubility of aspartame makes worse the degradation processes.

The method according to the invention permits the use of aspartame as starting material in respecting the constraints of purity that is required of a compound whose principal purpose is use in food.

It has in fact been noted that the quality of the product of the invention depends very heavily on the experimental conditions applied during the carrying out of the method. The nature of the catalyst, and to a lesser extent the time and the pressure of the hydrogenation, the nature of the reaction medium and its pH are thus revealed to be essential parameters.

In summary, the present invention describes a novel compound which possesses, as compared to aspartame, a sweetening potency 60 times greater and a greater stability in both neutral and acid media. Moreover, this novel compound is prepared directly and in one sole step from aspartame, in high yield and high purity.

The present invention will be described more completely with the aid of the following examples of preparation, which are not to be considered as limiting the scope of the invention.

EXAMPLE 1

In a reactor equipped with a stirrer assuring a very good transfer of gaseous hydrogen into the liquid phase, are introduced, with stirring, in this order: 60 cm$^3$ of a 0.1M aqueous solution of acetic acid, 1 g of platinum black (Aldrich No. 20,591-5: Platinum black), 2.55 g of 3,3-dimethylbutyraldehyde, 30 cm$^3$ of methanol and 5 g of aspartame.

After having purged the reactor with a current of nitrogen gas, the mixture is submitted to a hydrogenation at the relative pressure of 3 bars (0.3 MPa) at room temperature. The progress of the reaction is monitored by the removal of a crude sample and a determination of the formed product by high performance liquid chromatography (H.P.L.C.). The concentration of the desired product is determined by a comparison with an already established calibration curve. After 72 hours of hydrogenation, the formation of 97% of the expected product is observed.

The reaction is then interrupted by purging the reactor with a current of nitrogen gas and separating the catalyst by filtration on a fine filter (0.5 μm). If need be, the filtrate is adjusted to pH 5 by the addition of a few drops of a 1M solution of sodium hydroxide. The methanol is then evaporated in vacuo, the temperature being maintained at lower than 40° C. A white solid quickly precipitates. The mixture is further stirred for a few hours at room temperature in order to complete the precipitation. The product is separated by filtration, dried and washed with about 50 cm$^3$ of hexane 4.5 g of N-[N-(3,3-dimethylbutyl)-L-α-aspartyl]-L-hexahydrophenylalanine 1-methyl ester is finally obtained (yield 69%) as a white powder of high purity (greater than 98% by H.P.L.C.).

EXAMPLE 2

Using the same apparatus, the same solvent and the same reagents at the same concentrations as those described in Example 1, but using 1 g of platinum oxide as catalyst (Aldrich product No. 20,603-2: Platinum (IV) oxide, Adams' catalyst), in carrying out the hydrogenation at the relative pressure of 3 bars (0.3 MPa), always at room temperature, the reaction is stopped after 72 hours (96% of product formed). After purification by precipitation following the protocol described in Example 1, 4.5 g of expected product is obtained (yield 69%) as a white powder of very high purity (greater than 98% by H.P.L.C.).

The purity of the compound prepared following the method of the invention is monitored by the classical techniques of thin layer chromatography, infra-red spectroscopy, ultraviolet spectroscopy, high performance liquid chromatography (H.P.L.C.), thermal analysis, optical rotation, nuclear magnetic resonance and elemental analysis.

The physical criteria obtained for the compound prepared according to the invention are given hereafter.

Molecular formula: $C_{20}H_{36}N_2O_5$.

Molecular weight: 384.51.

Water content (Karl Fischer method): 3 to 5%.

Thin layer chromatography: Silica Gel 60 F254 on aluminium sheets (Merck No. 5554), eluent: butanol-acetic acid-water (8:2:2), detected with ninhydrin: $R_f$0.62.

Infra-red spectrum (KBr) $cm^{-1}$: 3514(HOH), 3367, 3195 (NH), 2957, 2920, 2850 (CH), 1755 ($COOCH_3$), 1659 (CONH), 1620–1593 ($COO^-$), 1450, 1388, 1199, 1177, 773.

Ultraviolet spectrum: maximum at 222 nm.

High performance liquid chromatography on a Merck column of "Lichrospher 100 RP-18 endcapped" type, 244 mm in length, 4 mm in diameter, eluent: ammonium acetate 65 mM-acetonitrile (50:50), flow: 1 ml/min, detector: refractometer, retention time: 4.9 min.

Differential thermal analysis from 40° to 350° C. at 10° C./min.: melting point 88° C., no decomposition at less than 200° C.

Optical rotation: $[\alpha]^D_{20}=-40°\pm1.25(c=2,$ methanol).

Nuclear magnetic resonance spectrum: (H, 200 MHz, DMSO-d6) 0.86 (s, 9H), 1.12–1.62 (m, 12H), 2.3–2.45 (m, 5H), 2.9 (m, 2H), 3.55 (m, 1H), 3.61 (s, 3H), 4.4 (m, 1H), 8.5 (d, 1H).

Elemental analysis: Found (Theoretical for 4.5% water): C 59.63 (59.78), H 9.15 (9.51), N 6.66 (6.97), O 23.35 (23.72).

The sweetening potency of the compound of the present invention has been evaluated by a group of eight experienced people. For this, the compound, in aqueous solution at varying concentrations, is compared, with respect to taste, to a control solution of sucrose of concentration 2%, 5%, or 10%. The sweetening potency of the test compound compared with sucrose then corresponds to the weight ratio between the compound and sucrose for equal sweetening intensity, i.e. when the sweet tastes of the solution of the test compound and the control solution of sucrose are considered by a majority of people to have the same sweetening intensity.

The sweetening potency of the compound of the invention corresponds approximately, on a weight basis, to 12,000 times that of sucrose by comparison with a 2% solution of sucrose, to 10,000 times by comparison with a 5% solution of sucrose and to 5,000 times by comparison with a 10% solution of sucrose.

The stability of the compound of the invention and aspartame was measured by determining, using high performance liquid chromatography, the amount of product remaining after an accelerated ageing of the solution by prolonged heating at 70° C. in a neutral medium (phosphate buffer at pH 7) or in an acid medium (phosphate buffer at pH 3). The stability of the compound thus tested is evaluated by its half-life ( time corresponding to 50% degradation).

Given in the annexed FIG. 1 is a comparative diagram of the stability curves of aspartame (curve a) compared with the compound of the invention (curve b) in acid medium at pH 3; the compound of the invention possesses a half-life of about 60 hours, whereas the half-life of aspartame under the same conditions is only 24 hours, which corresponds, for the compound of the invention, to a stability 2.5 times greater than that of aspartame.

Figure 2:
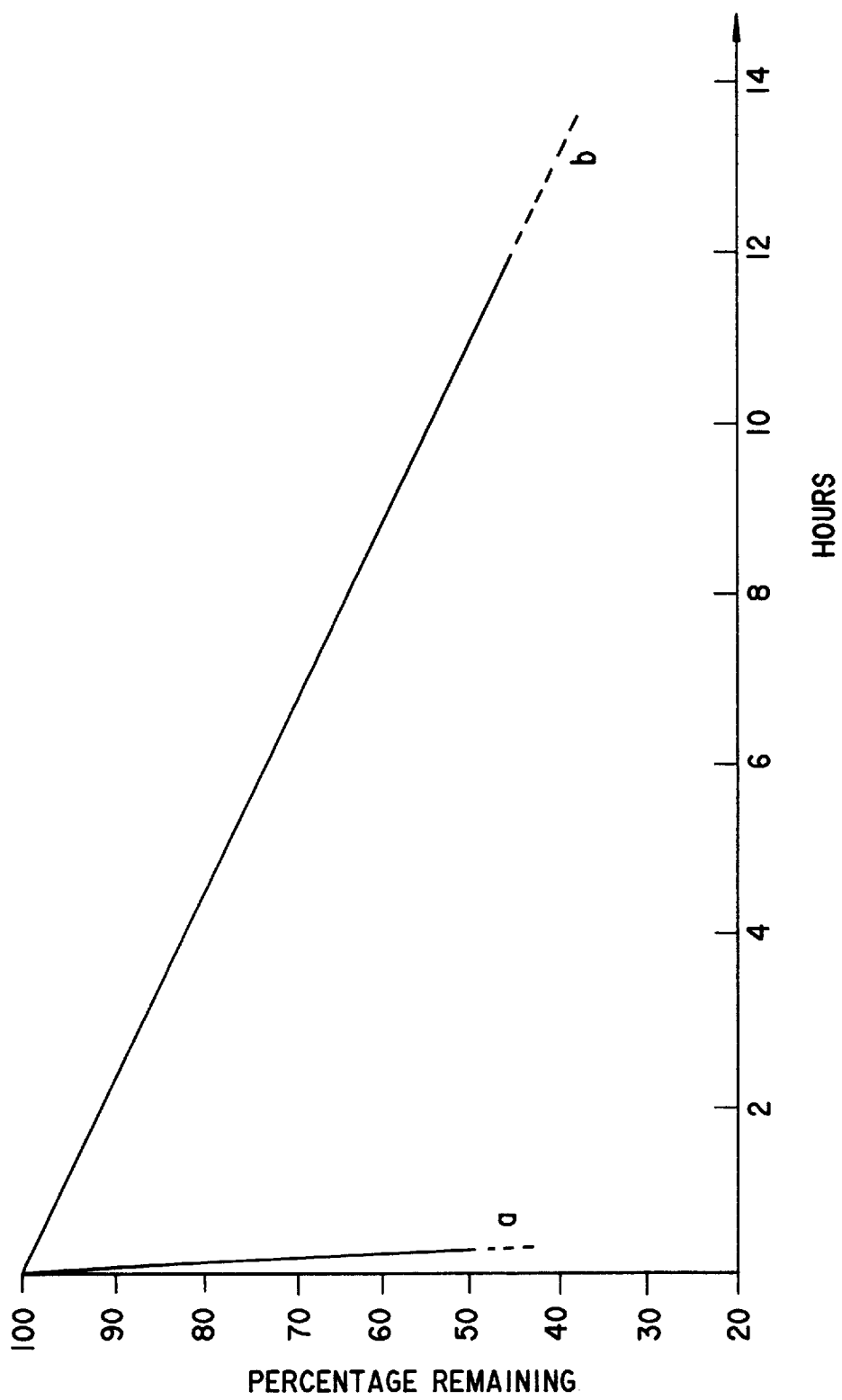

Given in the annexed FIG. 2 is a comparative diagram of the stability curve of aspartame (curve a) compared to the compound of the invention (curve b) at pH 7; the compound of the invention possesses a half-life of about 11 hours, whereas the half-life of aspartame under the same conditions is only 10 minutes, which corresponds, for the compound according to the invention, to a stability 66 times greater than that of aspartame.

We claim:

1. A sweetening compound characterized in that it is N-[N-(3,3-dimethylbutyl)-L-α-aspartyl]-L-hexahydrophenylalanine 1-methyl ester of formula:

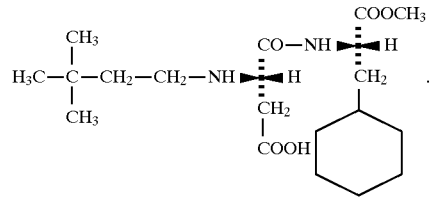

2. A method of preparation of N-[N-(3,3-dimethylbutyl)-L-α-aspartyl]-L-hexahydrophenylalanine 1-methyl ester of formula:

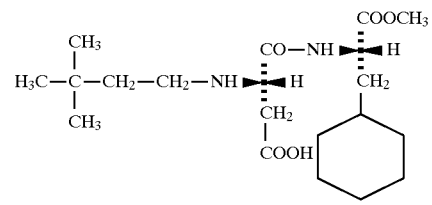

characterized in that a solution of aspartame and 3,3-dimethylbutyraldehyde at room temperature is treated with hydrogen at a relative pressure of 3 bars in the presence of a catalyst based on platinum.

3. A method according to claim 2 characterized in that the catalyst is platinum black or platinum oxide.

4. A method according to claim 3 wherein the product formed is purified by precipitation and filtration, after the evaporation in vacuo of the alcohol part of the solvent.

5. A method according to claim 3 wherein the concentration of aspartame in the aqueous/alcohol solution is between 50 and 60 g/l and the concentration of 3,3-dimethylbutyraldehyde is between 20 and 30 g/l.

6. A method according to claim 5 wherein the product formed is purified by precipitation and filtration, after the evaporation in vacuo of the alcohol part of the solvent.

7. A method according to claim 3 wherein the solution of aspartame and 3,3-dimethylbutyraldehyde is an aqueous/ alcohol solution of pH 4.5–5 obtained by mixing a 0.1M solution of acetic acid and methanol.

8. A method according to claim 7 wherein the product formed is purified by precipitation and filtration, after the evaporation in vacuo of the alcohol part of the solvent.

9. A method according to claim 7 wherein t aqueous/alcohol solution is between 50 and 60 g/l and the concentration of 3,3-dimethylbutyraldehyde is between 20 and 30 g/l.

10. A method according to claim 9 wherein the product formed is purified by precipitation and filtration, after the evaporation in vacuo of the alcohol part of the solvent.

11. A method according to claim 2 wherein the solution of aspartame and 3,3-dimethylbutyraldehyde is an aqueous/alcohol solution of pH 4.5–5 obtained by mixing a 0.1M solution of acetic acid and methanol.

12. A method according to claim 11 wherein the product formed is purified by precipitation and filtration, after the evaporation in vacuo of the alcohol part of the solvent.

13. A method according to claim 11 wherein the concentration of aspartame in the aqueous/alcohol solution is between 50 and 60 g/l and the concentration of 3,3-dimethylbutyraldehyde is between 20 and 30 g/l.

14. A method according to claim 13 wherein the product formed is purified by precipitation and filtration, after the evaporation in vacuo of the alcohol part of the solvent.

15. A method according to claim 2 wherein the concentration of aspartame in the aqueous/alcohol solution is between 50 and 60 g/l and the concentration of 3,3-dimethylbutyraldehyde is between 20 and 30 g/l.

16. A method according to claim 15 wherein the product formed is purified by precipitation and filtration, after the evaporation in vacuo of the alcohol part of the solvent.

17. A method according to claim 2 wherein the product formed is purified by precipitation and filtration, after the evaporation in vacuo of the alcohol part of the solvent.

* * * * *